United States Patent [19]
Renfroe

[11] Patent Number: 4,539,410
[45] Date of Patent: * Sep. 3, 1985

[54] N-SUBSTITUTED-2-(1-IMIDAZOLYL)IN-DOLES

[75] Inventor: Harris B. Renfroe, West Nyack, N.Y.

[73] Assignee: Ciba Geigy Corporation, Ardsley, N.Y.

[ * ] Notice: The portion of the term of this patent subsequent to Mar. 13, 2001 has been disclaimed.

[21] Appl. No.: 565,936

[22] Filed: Dec. 27, 1983

Related U.S. Application Data

[63] Continuation-in-part of Ser. No. 430,644, Sep. 30, 1982, Pat. No. 4,436,746.

[51] Int. Cl.³ ............................................ C07D 403/04
[52] U.S. Cl. .................................... 548/336; 548/252; 548/253; 548/254
[58] Field of Search ................ 548/252, 253, 254, 336

[56] References Cited

U.S. PATENT DOCUMENTS

| 3,454,586 | 7/1969 | Suh | 548/336 X |
| 4,059,583 | 11/1977 | McComsey et al. | 548/336 X |
| 4,139,634 | 2/1979 | Pigerol et al. | 548/469 X |
| 4,140,858 | 2/1979 | Zinnes et al. | 548/336 |
| 4,217,357 | 8/1980 | Cross et al. | 424/273 R |
| 4,273,782 | 6/1981 | Cross et al. | 424/273 R |
| 4,436,746 | 3/1984 | Renfroe | 424/273 R |
| 4,448,784 | 5/1984 | Glamkowski et al. | 548/469 X |

FOREIGN PATENT DOCUMENTS

| 2424912 | 11/1979 | France | 548/341 |
| WO82/04047 | 11/1982 | PCT Int'l Appl. | 544/141 |

OTHER PUBLICATIONS

Abstracts, North American Medicinal Chemistry Symposium, Toronto, (1982), p. 68.
R. L. N. Harris, *Aust. J. Chem.* (1974), vol. 27, p. 2642.

*Primary Examiner*—Richard A. Schwartz
*Attorney, Agent, or Firm*—Norbert Gruenfeld

[57] ABSTRACT

Various 1-carboxylic acid substituted-2-(1-imidazolyl-)indoles and functional derivatives thereof are highly specific thromboxane synthetase inhibitors. Synthesis of, pharmaceutical compositions thereof, methods of treatment utilizing such compounds and intermediates for their synthesis are included.

9 Claims, No Drawings

N-SUBSTITUTED-2-(1-IMIDAZOLYL)INDOLES

CROSS-REFERENCE TO RELATED APPLICATION

This is a continuation-in-part of application Ser. No. 430,644 filed Sept. 30, 1982, now U.S. Pat. No. 4,436,746.

The present invention is concerned with N-(or 1)-substituted-2-(1-imidazolyl)indoles of formula I representing a novel class of pharmaceuticals. For example, the compounds of formula I are surprisingly potent and highly specific thromboxane synthetase inhibitors.

The foregoing attributes render the N-substituted-2-(1-imidazolyl)indoles of this invention particularly useful when administered, alone or in combination, to mammals, e.g. for the treatment or prevention of diseases responsive to the inhibition of thromboxane synthetase, comprising cardiovascular disorders such as thrombosis, atherosclerosis, coronary spasm, cerebral ischaemic attacks, migraine and other vascular headaches, myocardial infarction, angina pectoris, hypertension; respiratory disorders, such as asthma; and inflammatory disorders. Inhibition of thromboxane synthetase also has been noted to decrease metastasis in certain classes of tumors, and the compounds of this invention may thus be useful for the treatment of certain carcinomas.

This invention relates to N(or 1)-substituted-2-(1-imidazolyl)indoles of formula I which are useful as selective thromboxane synthetase inhibitors, processes for preparing same, pharmaceutical compositions comprising said compounds, and methods of treating syndromes, conditions and diseases in mammals responsive to the inhibition of thromboxane synthetase by administration of said compounds and compositions.

This invention concerns new 1-substituted 2-(1-imidazolyl)-indoles of formula I

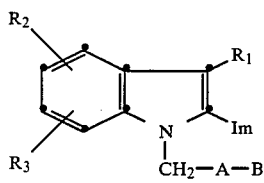
(I)

wherein $R_1$ represents hydrogen or lower alkyl; Im represents 1-imidazolyl unsubstituted or substituted by lower alkyl, carboxy, lower alkoxycarbonyl or carbamoyl; $R_2$ and $R_3$ independently represent hydrogen, lower alkyl, halogen, trifluoromethyl, hydroxy, lower alkoxy, lower alkyl-(thio, sulfinyl or sulfonyl); or $R_2$ and $R_3$ together when attached to adjacent carbons represent lower alkylenedioxy; A represents alkylene of 1 to 12 carbon atoms, alkenylene of 2 to 12 carbon atoms, alkynylene of 2 to 12 carbon atoms, lower alkylenephenylene-lower alkylene, lower alkylenephenylene, phenylene-lower alkylene, phenylene, a direct bond, lower alkylene-(thio or oxy)-lower alkylene, (thio- or oxy)-phenylene, lower alkylene-(thio- or oxy)-phenylene, phenylene-(thio or oxy)-lower alkylene or phenylene-lower alkenylene; B represents carboxy, lower alkoxycarbonyl, carbamoyl, mono- or di-lower alkylcarbamoyl, cyano, hydroxymethyl, hydroxycarbamoyl, 5-tetrazolyl or formyl; the N-oxides thereof; and salts, especially pharmaceutically acceptable salts thereof.

Preferred embodiments of the invention relate to the 1-substituted 2-(1-imidazolyl)-indoles of formula I wherein $R_1$ represents hydrogen or lower alkyl; Im represents 1-imidazolyl unsubstituted or substituted by lower alkyl, carboxy, lower alkoxycarbonyl or carbamoyl; $R_2$ and $R_3$ independently represent hydrogen, lower alkyl, halogen, trifluoromethyl, hydroxy, lower alkoxy, lower alkyl-(thio, sulfinyl or sulfonyl); or $R_2$ and $R_3$ together when attached to adjacent carbons represent lower alkylenedioxy; A represents alkylene of 1 to 12 carbon atoms, alkenylene of 2 to 12 carbon atoms, alkynylene of 2 to 12 carbon atoms, lower alkylenephenylene-lower alkylene, lower alkylenephenylene, phenylene lower alkylene, phenylene, a direct bond, lower alkylene-(thio or oxy)-lower alkylene, lower alkylene-(thio or oxy)-phenylene; B represents carboxy, lower alkoxycarbonyl, carbamoyl, mono- or di-lower alkylcarbamoyl, cyano or hydroxymethyl; the N-oxides thereof; and salts, especially pharmaceutically acceptable salts thereof.

Further preferred embodiments of this invention relate to compounds of formula I wherein $R_1$ represents hydrogen or lower alkyl; Im represents 1-imidazolyl unsubstituted or substituted by lower alkyl; $R_2$ is hydrogen, lower alkyl, halogen, trifluoromethyl, hydroxy, lower alkoxy; $R_3$ is hydrogen; A represents alkylene of 1 to 12 carbon atoms, phenylene, lower alkylenephenylene or lower alkylene-(thio or oxy)-phenylene of 7 to 10 carbon atoms each, or a direct bond; B represents carboxy, lower alkoxycarbonyl, carbamoyl, cyano or hydroxymethyl; the N-oxides thereof; and salts, especially pharmaceutically acceptable salts thereof.

Particularly preferred are said compounds wherein $R_2$ is attached at the 5-position of the indole nucleus.

Very useful are compounds of formula I wherein A represents alkylene of 1 to 12 carbon atoms.

Particularly useful are compounds of formula II

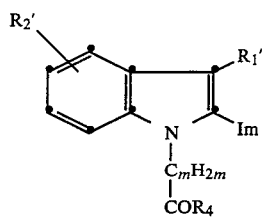
(II)

wherein $R_1'$ represents hydrogen or lower alkyl; $R_2'$ represents hydrogen, lower alkyl, halogen, trifluoromethyl, hydroxy or lower alkoxy; Im represents 1-imidazolyl; m represents an integer from 1 to 13; $R_4$ represents hydroxy, lower alkoxy or amino; and salts, especially pharmaceutically acceptable salts thereof.

Especially valuable are compounds of formula II wherein $R_1'$ represents methyl, ethyl, propyl; $R_2'$ represents hydrogen, methyl, chloro, fluoro, trifluoromethyl, hydroxy or methoxy; m represents an integer from 3 to 10; $R_4$ represents hydroxy, ethoxy, methoxy or amino; Im represents 1-imidazolyl; and salts, especially pharmaceutically acceptable salts thereof.

Most preferred are the compounds of formula II wherein $R_1'$ represents methyl, $R_2'$ represents hydrogen, m is 4 to 8, Im represents 1-imidazolyl, and $R_4$ represents hydroxy, ethoxy, methoxy or amino, and salts, especially pharmaceutically acceptable salts thereof.

Also valuable are compounds of formula III

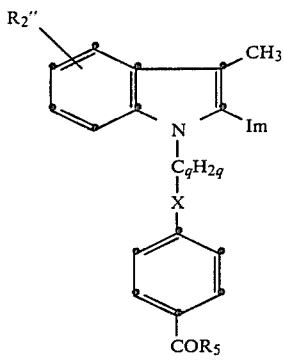 (III)

wherein $R_2''$ represents hydrogen, lower alkyl, halogen, trifluoromethyl, hydroxy or lower alkoxy; q represents an integer from 1 to 4; x is oxygen, sulfur or a direct bond; $R_5$ represents hydroxy or lower alkoxy; Im represents 1-imidazolyl; and salts, especially pharmaceutically acceptable salts thereof.

Preferred are compounds of formula III wherein $R_2''$ represents hydrogen, methyl, chloro, fluoro, trifluoromethyl, hydroxy or methoxy.

Further preferred are compounds of formula III wherrein q is 1; Im represents 1-imidazolyl; $R_5$ is hydroxy; and X is a direct bond. Also further preferred are compounds of formula III wherein q is 2; $R_5$ is OH, and X represents O or S.

The general definitions used herein have the following meanings within the scope of the present invention.

Alkylene of 1 to 12 carbon atoms, represents straight chain or branched alkylene, preferably propylene, butylene, pentylene, hexylene or heptylene, said radicals being unsubstituted or substituted by one or more lower alkyl groups, with the proviso that the total number of carbon atoms equals no more than 12.

Alkenylene of 2 to 12 carbon atoms represents straight chain or branched alkenylene, preferably propenylene, 1- or 2-butenylene, 1- or 2-pentenylene, 1-, 2- or 3-hexenylene, 1-, 2-, 3- or 4-heptenylene, said groups being unsubstituted or substituted by one or more lower alkyl groups, with the proviso that the total number of carbon atoms equals no more than 12.

Alkynylene of 2 to 12 carbon atom represents straight chain or branched alkynylene, preferably propynylene, 1- or 2-butynylene, 1- or 2-pentynylene, 1-, 2- or 3-hexynylene, 1-, 2-, 3- or 4-heptynylene, said radicals being unsubstituted or substituted by one or more lower alkyl groups, with the proviso that the total number of carbon atoms equals no more than 12.

The term phenylene represents 1,2-, 1,3- and preferably 1,4-phenylene.

The term "lower" when referred to above and hereinafter in connection with organic groups, radicals or compounds respectively defines such as with up to and including 7, preferably up to and including 4 and advantageously one, two or three carbon atoms.

A lower alkylenephenylene group, a phenylene lower alkylene group, a lower alkylenephenylene-lower alkylene group, a lower alkylene-(thio or oxy)-phenylene group, a phenylene-(thio or oxy)-lower alkylene group, or a phenylene-lower alkenylene group preferably contains 1 to 4 carbon atoms and advantageously one or two carbon atoms in each alkylene or alkenylene portion. The lower alkylene and alkenylene portions may be straight chain or branched.

A lower alkylene-(thio or oxy)-lower alkylene group is straight chain or branched and may contain a total of 2 to 12 carbon atoms, preferably 2 to 8 carbon atoms.

A lower alkyl group preferably contains 1–4 carbon atoms and represents for example ethyl, propyl, butyl or advantageously methyl.

A lower alkylenedioxy group represents preferably ethylenedioxy and methylenedioxy.

A lower alkoxy group preferably contains 1-4 carbon atoms and represents for example, ethoxy, propoxy or advantageously methoxy. A lower alkyl-(thio, sulfinyl or sulfonyl) group represents advantageously methylthio, methylsulfinyl or methylsulfonyl respectively.

A lower alkoxycarbonyl group preferably contains 1–4 carbon atoms in the alkoxy portion and represents for example; methoxycarbonyl, propoxycarbonyl, isopropoxycarbonyl or advantageously ethoxycarbonyl. A mono(lower alkyl)-carbamoyl group preferably contains 1–4 carbon atoms in the alkyl portion and is for example N-methylcarbamoyl, N-propylcarbamoyl, or advantageously N-ethylcarbamoyl. A di(lower alkyl)-carbamoyl group preferably contains 1–4 carbon atoms in each lower alkyl portion and represents for example N,N-dimethylcarbamoyl, N-methyl-N-ethylcarbamoyl and advantageously N,N-diethylcarbamoyl.

Halogen is preferably fluorine and chlorine, but may also represent bromine or iodine.

Salts are preferably pharmaceutically acceptable salts, e.g. metal or ammonium salts of said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono-, di- or tri-lower(alkyl, cycloalkyl or hydroxyalkyl)-amines, lower alkylenediamines or (hydroxy-lower-alkyl or aryl-lower alkyl)-alkylammonium bases, e.g., methylamine, diethylamine, triethylamine, dicyclohexylamine, triethanolamine, ethylenediamine, tris-(hydroxymethyl)-aminomethane or benzyl-trimethylammonium hydroxide. Said compounds of formula I form acid addition salts, which are preferably such of pharmaceutically acceptable inorganic or organic acids, such as of strong mineral acids, for example hydrohalic, e.g. hydrochloric or hydrobromic acids; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, maleic, fumaric, pyruvic, phenylactic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid, or ascorbic acid.

The compounds of this invention exhibit valuable pharmacological properties, e.g. cardiovascular effects, by selectively decreasing thromboxane levels through selective inhibition of thromboxane synthetase in mammals. The compounds are thus useful for treating diseases responsive to thromboxane synthetase inhibition in mammals, primarily cardiovascular disorders such as thrombosis, atherosclerosis, coronary spasm, cerebral ischaemic attacks, migraine and other vascular headaches, myocardial infarction, angina pectoris and hypertension.

These effects are demonstrable in in vitro tests or in vivo animal tests using advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 to 100 mg/kg/day, preferably between about 0.05 and 50 mg/kg/day, advantageously between about 0.1 and 25 mg/kg/day.

The in vitro inhibition of the thromboxane synthetase enzyme can be demonstrated, analogous to the method of Sun, Biochem. Biophys. Res. Comm. 74, 1432 (1977); the testing procedure is as follows:

$^{14}C$-Arachidonic acid is incubated with an enzyme mixture preparation consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin $E_2$ (PGE$_2$) is reduced to a mixture of Prostaglandin $F_2\alpha$ and $F_2\beta$ (PGF2 $\alpha+\beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene:acetone:glacial acetic acid (100 volumes:100 volumes:3 volumes). The radioactive zones are located; those corresponding to Thromboxane $B_2$ ($T\times B_2$) and PGF$_2$ $\alpha+\beta$ are transferred to liquid scintillation vials and counted. The ratio of counts for $T\times B_2/PGF_2 \alpha+\beta$ is calculated for each concentration of test compound and IC$_{50}$ values are determined graphically as the concentration of test compound at which the ratio of $T\times B_2/PGF_2 \alpha+\beta$ is reduced to 50% of the control value.

The in-vitro effect on prostaglandin cyclooxygenase is measured by a modification of the method of Takeguchi et al. described in Biochemistry 10, 2372 (1971); the testing procedure is as follows:

Lyophilized sheep seminal vesicle microsomes are utilized as the prostaglandin-synthesizing enzyme preparation. The conversion of $^{14}C$-arachidonic acid to PGE$_2$ is measured. Test compounds (dissolved in buffer, or if necessary, in a small amount of ethanol) are added to the incubation mixture. The prostaglandins are extracted and separated by thin-layer chromatography; the plates are scanned, the radioactive zones corresponding to PGE$_2$ are transferred to liquid scintillation vials and counted for radioactivity. IC$_{50}$ values for inhibition are determined graphically as the concentration of test compound causing a 50% reduction in the amount of PGE$_2$ synthesized.

The in-vitro effect on prostacyclin (PGI$_2$) synthetase is measured analogous to the method of Sun et al., Prostaglandins 14, 1055 (1977). The testing procedure is as follows:

$^{14}C$-Arachidonic acid is incubated with an enzyme mixture consisting of solubilized and partially purified prostaglandin cycle-oxygenase from sheep seminal vesicles and crude PGI$_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described by Sun et al. The radioactive zones are located with a scanner; those corresponding to 6-keto-PGF$_1\alpha$(a stable end product of prostacyclin biotransformation) and PGE$_2$ are transferred to liquid scintillation vials and counted. The ratio of counts for 6keto-PGF$_1\alpha$/PGE$_2$ is calculated for each concentration of test compounds used. IC$_{50}$ values for inhibition are determined graphically as the concentration of test compound at which the ratio of 6-keto-PGF$_1\alpha$/PGE$_2$ is reduced to 50% of the control value.

The inhibition of the synthesis and the reduction of plasma levels of thromboxane is determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with inophore A23187 (0.5 mg/kg) two hours later. Blood is collected for analysis 2 minutes after the ionophore injection. A single aliquot of each plasma sample is assayed for thromboxane $B_2$ and another aliquot for 6-keto-PGF$_1\alpha$, the stable metabolites of thromboxane $A_2$ and prostacyclin (PGI$_2$) respectively, by radioimmunoassay.

Compounds of the formula I are very potent and selective thromboxane synthetase inhibitors. At and above the effective dose levels for thromboxane synthetase inhibition neither the beneficial prostacyclin synthetase enzyme system nor the prostaglandin cyclooxygenase enzyme system is significantly inhibited.

Illustrative of the invention, the IC$_{50}$ for 1-(5-carboxypentyl)-3-methyl-2-(1-imidazolyl)indole hydrochloride is $2.3\times10^{-9}M$ for thromboxane synthetase inhibition.

Further illustrative of the invention, 1-(5-carboxypentyl-3-methyl-2-(1-imidazolyl)-indole hydrochloride decreases the plasma concentration of thromboxane $B_2$ by over 50% in the rats at an oral dose as low as 0.20 mg/kg; an increase in the plasma level of prostacyclin occurs at this or a higher dose thereof.

The aforementioned advantageous properties render the compounds of this invention of great value as specific therapeutic agents for the treatment of diseases responsive to the inhibition of thromboxane synthetase in mammals including man, e.g. for the treatment of cardiovascular diseases such as thromboembolism.

In addition to the pharmaceutically acceptable salts cited above, any prodrug derivatives thereof, e.g., pharmaceutically acceptable esters and amides of the carboxylic acids of this invention that may be convertible by solvolysis or under physiological conditions to the said carboxylic acids, represent a further object of this invention.

Said esters are preferably e.g., the straight chain or branched lower alkyl esters unsubstituted or suitably substituted such as the pivaloyloxymethyl, 2-diethylaminoethyl, α-carboxyethyl or suitably esterified α-carboxyethyl esters and the like which are prepared by methods well known to the art.

Said amides are preferably e.g. simple primary and secondary amides and amides derived from the amino acids or derivatives thereof, such as the amides derived from alanine, phenylalanine and the like.

The compounds of formula I are advantageously prepared, according to the following processes:

(1) Condensing a compound of the formula IV

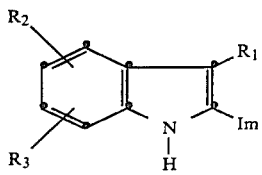
(IV)

wherein R₁, R₂, R₃ and Im have meaning as previously defined; with a reactive functional derivative of a compound of the formula V

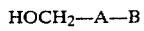
HOCH₂—A—B    (V)

wherein A and B have meaning as previously defined, or (2) condensing a compound of the formula VI

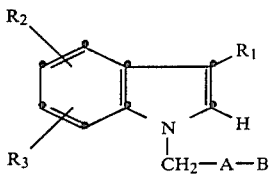
(VI)

wherein R₁–R₃, A and B have meaning as previously defined; with a compound of the formula ImH, wherein Im has meaning as previously defined; or (3) decarboxylatng a compound of the formula (VII)

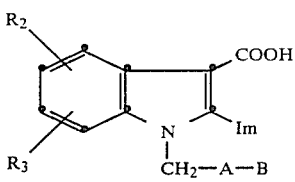
(VII)

in which R₂, R₃ and Im have meaning as previously defined; or (4) converting into a compound of formula I a compound of formula Ia

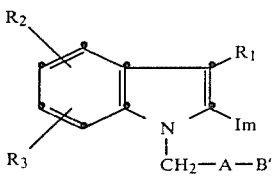
(Ia)

wherein A, Im, R₁, R₂ and R₃ have meaning as previously defined and B′ represents a group convertible into B with optional extension of the chain A within its definition; and if desired or necessary, temporarily protecting in each of these processes an interfering reactive group; and, if desired, converting any resulting compound of formula I into another compound of the invention; and/or, if desired, converting a resulting free compound into a salt or a resulting salt into the free compound or into another salt; and, if required, resolving a mixture of isomers or racemates obtained into the single isomers or racemates; and, if required, resolving a racemate obtained into the optical antipodes.

The condensation according to process (1) is preferably carried out under basic conditions, e.g. with a basic alkali metal salt or a quaternary ammonium salt such as tetrabutyl ammonium chloride. For example, compounds of formula IV are converted preferably in situ, to reactive organometallic intermediates with a reactive metallizing agent, preferably about one molar equivalent of e.g. a strong alkali metal base, such as lithium diisopropylamide, sodium hydride, potassium t-butoxide, in an inert solvent such as dimethylformamide or tetrahydrofuran, at a temperature range between −50° to +75°, preferably between −25° and +50°. Condensation of the resulting reactive organometallic compound of formula IV with a reactive functional derivative of a compound of formula V proceeds at a temperature range from about −25° to +50° C., preferably at a temperature range of 0° to 30° C. In the case where B represents carboxy, carbamoyl, hydroxycarbamoyl, or mono lower alkylcarbamoyl, additional, e.g. one molar equivalent, of metallizing agent is required.

The novel intermediates of formula IV are advantageously prepared by condensation of the corresponding 2-unsubstituted indole of formula VIII

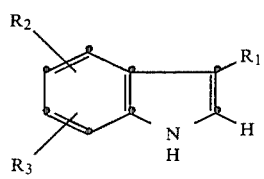
(VIII)

wherein R₁, R₂ and R₃ have meaning as previously described, with a compound of the formula ImH, wherein Im has meaning as previously described, in the presence of a halogen, preferably bromine in an inert solvent, such as dioxane, at a temperature range of 0° to 100°, advantageously at room temperature.

The starting materials of formula V and Va are known or if new, are prepared according to conventional methods, e.g. the methods illustrated in U.S. Pat. No. 4,256,757, British patent application No. 2,016,452A or as described in the examples herein.

The indoles of formula VIII are known or if new are prepared by conventional methods well known in the art and as illustrated herein.

The condensation according to process (2) is carried out in a fashion analogous to the condition described above for the preparation of intermediates of formula IV. Process (2) is most useful for the preparation of compounds of formula I wherein R₁ is lower alkyl and A does not contain a group reactive with halogen, e.g. carbon to carbon double bond.

The starting materials of formula VI can be prepared by condensation of an indole of formula VIII with a reactive functional derivative of a compound of formula V as described above for the analogous condensation under process (1).

The decarboxylation according to process (3) is carried out in a conventional manner, e.g. with heat in an inert high boiling solvent or in the presence of a strong acid, e.g. a mineral acid such as hydrochloric acid. Said process is useful for the preparation of compounds of formula I wherein $R_1$ is hydrogen.

The starting 3-carboxy-substituted indoles of formula VII may be prepared according to the methodology described above in process (1), e.g. by reacting an indole of general formula IV, wherein $R_1$ now is carboxy or a group from which carboxy can be generated, (such as esterified carboxy, optionally esterified hydroxymethyl) with a reactive functional derivative of a compound of formula V.

The N-unsubstituted indole starting materials of general formula IV, wherein $R_1$ represents carboxy or a group from which carboxy can be generated, can be prepared by treatment of the 2-unsubstituted compound of general formula VIII, wherein $R_1$ now represents carboxy or a group from which carboxy can be generated, with a compound of the formula Im—H using methodology described hereinabove.

The conversion of a compound of formula Ia according to process (4), wherein B' differs from B, into a compound of formula I, and the optional conversion of resulting product of formula I into another compound of this invention are performed by chemical methodology known to the art, and/or e.g. as described herein.

Convertible group B' preferably represents trialkoxymethyl, esterified hydroxymethyl such as halomethyl, etherified hydroxymethyl, 2-oxazolinyl, dihydro-2-oxazolinyl, lower alkanoyloxymethyl, acetyl, carboxycarbonyl, trihaloacetyl, di(lower)alkoxymethyl, alkylenedioxymethyl, vinyl, alkynyl, esterified carboxy, amidated carboxy.

The intermediates of formula Ia are prepared according to processes 1 to 3 and/or as described herein, using conventional chemical methodology well known to the art, e.g. according to process (1) by condensing a compound of formula IV with a reactive functional derivative of a compound of formula Va HOCH$_2$—A—B'      (Va)

wherein A and B' have meaning as defined above.

A specific embodiment of the invention comprises converting a compound of formula I wherein B is not carboxy into a compound of formula I wherein B represents carboxy and optionally extending group A within its definition.

Groups convertible into a carboxy group are, for example, esterified carboxy groups, carboxy groups in form of their anhydrides, including corresponding groups of asymmetrical and inner anhydrides, amidated carboxy groups, cyano, amidino groups, including cyclic amidino group such as 5-tetrazolyl, iminoether groups, including cyclic iminoether groups, e.g., 2-oxazolinyl or dihydro-2-oxazolinyl groups substituted by lower alkyl, and also hydroxymethyl, etherified hydroxymethyl, lower alkanoyloxymethyl, trialkoxymethyl, acetyl, trihaloacetyl, halomethyl, carboxycarbonyl (COCOOH), formyl (CHO), di(lower)alkoxymethyl, alkylenedioxymethyl, vinyl, ethynyl or diazoacetyl.

Said interconversions to the compounds of formula I wherein B represents carboxy are carried out by methods well-known to the art and described herein.

Certain terms used in the processes have the meanings as defined below.

Reactive functional derivatives of alcohols of formula V and Va are e.g. such esterified by a strong inorganic or organic acid, above all a hydrohalic acid, e.g. hydrochloric, hydrobromic or hydriodic acid, an aliphatic or aromatic sulfonic acid, e.g. methanesulfonic acid, p-toluenesulfonic acid, and are prepared by methods known in the art.

Trialkoxymethyl represents preferably tri(lower alkoxy)-methyl, particularly triethoxy- or trimethoxymethyl.

Etherified hydroxymethyl represents preferably tertiary lower alkyloxymethyl, lower alkoxyalkoxymethyl such as methoxymethyloxymethyl, 2-oxa- or 2-thiacycloalkoxymethyl, particularly 2-tetrahydropyranyloxymethyl.

Esterified hydroxymethyl represents preferably lower alkanoyloxymethyl, e.g. acetyloxymethyl.

Halomethyl represents especially chloromethyl but may also be bromomethyl or iodomethyl.

An alkali metal represents preferably lithium buty may also be potassium or sodium.

Esterified carboxy groups are preferably in form of the lower alkyl esters, e.g. the methyl, ethyl, n- or i-(propyl or butyl) esters; substituted lower alkyl esters e.g. the ω-amino, ω-mono- or dimethylamino, α-carboxy or α-carbethoxy-(ethyl, propyl or butyl) esters; aryl(lower)alkyl esters, e.g. benzyl, (methyl-, methoxy-, chloro-)substituted benzyl, and pyridylmethyl esters; lower alkanoyloxy-(lower)alkyl esters, e.g. pivaloyloxymethyl esters; 3-phthalidyl and (methyl-, methoxy-, chloro-)substituted 3-phthalidyl esters, derived from the corresponding 3-hydroxyphthalides, (hydroxy-, lower alkanoyloxy-, lower alkoxy-) substituted lower alkoxymethyl esters e.g. β-(hydroxy-, acetyloxy-, methoxy-)ethoxymethyl esters; bicycloalkyloxy-carbonyl-(lower) alkyl esters, e.g. those derived from bicyclic monoterpenoid alcohols, such as unsubstituted or lower alkyl substituted bicyclo [2,2,1]heptyloxycarbonyl-(lower)alkyl esters, advantageously bornyloxycarbonylmethyl esters; halo substituted lower alkyl esters, e.g. trichloroethyl or iodoethyl esters.

Amidated carboxy groups are preferably carboxy groups in form of their unsubstituted amides; N-mono or di-lower alkylamides, e.g. mono- or di-methylamides; tertiary amides derived from e.g. pyrrolidine, piperidine or morpholine; α-(carbo loweralkoxy)- or carboxy-substituted lower alkylamides, e.g. mono N-(carboethoxymethyl)-amides, and mono N-(carboxymethyl)-amides; α-(carbo loweralkoxy)- or carboxy-substituted aryl(lower) alkylamides, e.g. (carboethoxy or carboxy) substituted phenethylamides; amino(lower)-alkylamides, e.g. β-aminoethylamides and β-(carbobenzyloxy-amino)-ethylamides.

The conversion into the carboxy group is accomplished by methods which are known per se, and as described herein and in the examples, e.g., by solvolysis such as hydrolysis or acidolysis as previously described, or by reduction (esterified carboxy groups). For example, a trichloroethyl or 2-iodoethyl ester may be converted into the carboxylic acid by reduction, e.g. with zinc and a carboxylic acid in the presence of water. Benzyl esters or nitrobenzyl esters may be converted into the carboxy group by catalytic hydrogenation, the latter also with chemical reducing agents, e.g., sodium dithionite or with zinc and a carboxylic acid. In addition, tert-butyl esters may also be cleaved with trifluoroacetic acid. During the reduction an alkenylene or alkynylene chain A may be converted into the corresponding alkylene chain.

Furthermore, compounds of formula Ia wherein B' represents acetyl may be oxidatively cleaved to the corresponding compounds of formula I wherein B represents carboxy by conversion first to a compound of formula Ia wherein B' represents trihaloacetyl, e.g. tribromo or triiodoacetyl, by treatment e.g. with sodium hypobromite followed by cleavage with e.g. an aqueous base, such as sodium hydroxide.

The starting materials of formula Ia wherein B' represents acetyl are in turn prepared from compounds of formula Ia wherein B' represents halomethyl by treatment with an alkyl ester of acetoacetic acid, e.g. ethyl acetoacetate, in the presence of a base, e.g. sodium hydride, followed by hydrolysis with a strong base, e.g., aqueous sodium hydroxide.

Said compounds are also prepared by condensing a compound of formula Ia wherein B' is cyano with e.g. a Grignard or other organometallic reagent, e.g. methyl magnesium bromide under standard conditions.

Compounds of formula Ia wherein B' represents carboxycarbonyl (COCOOH) are converted thermally or by oxidation to compounds of formula I wherein B represents carboxy by heating at elevated temperature e.g., at about 200 degrees, in the presence of glass powder, or by treating e.g., with hydrogen peroxide in the presence of a basic agent, e.g. sodium hydroxide.

The starting materials of formula Ia wherein B' represents COCOOH are prepared by e.g. condensation of a compound of formula Ia wherein B' represents halomethyl with e.g. 2-ethoxy-carbonyl-1,3-dithiane, and subsequent oxidative hydrolysis, e.g. with N-bromosuccinimide in aqueous acetone followed by treatment with dilute aqueous sodium hydroxide.

Compounds of formula Ia wherein B' represents formyl, di(lower)alkoxymethyl or alkylenedioxymethyl (formyl protected in the form of an acetal), e.g. the dimethyl acetal, are oxidized with e.g. silver nitrate, pyridinium dichromate or ozone to the corresponding compound of formula I wherein B represents carboxy.

Compounds of formula Ia wherein B' represents vinyl may be converted to compounds of formula I wherein B represents carboxy by first ozonolysis to compounds of formula I wherein B represents formyl, which are in turn oxidized to compounds of formula I wherein B represents carboxy.

Compounds of formula Ia wherein B' represents vinyl may also be treated with nickel carbonyl and carbon monoxide under high pressure conditions to give compounds of formula I wherein B represents carboxy and the chain A contains a double bond adjacent to the carboxyl group.

Compounds of formula Ia wherein B' represents ethynyl may be treated with a strong base, e.g. butyl lithium followed by condensation with carbon dioxide or condensation with a lower alkyl haloformate, e.g. ethyl chloroformate followed by hydrolysis to give compounds of formula I wherein B represents carboxy and the chain A contains a triple bond adjacent to the carboxyl group.

Compounds of formula Ia wherein B' represents halomethyl may be converted to a corresponding organometallic intermediate, e.g. a cuprous or magnesium derivative, under conditions well known to the art.

Condensation of e.g. the resulting organomagnesium (Grignard) reagent, e.g. a compound of formula Ia wherein B' is transformed to e.g. CH$_2$MgCl, with carbon dioxide yields of a compound of formula I wherein B represents carboxy and the chain has been extended by 1 carbon atom.

Condensation of said Grignard reagent with e.g. a lower alkyl haloacetate or e.g. ethyl bromoacetate and subsequent hydrolysis yields a compound of formula I wherein B represents carboxy and wherein the chain has been extended by 2 carbon atoms.

Said Grignard reagent may be condensed in the presence of a cuprous halide, e.g. cuprous chloride, with an α,β-unsaturated acid, e.g. propiolic or acrylic acid to yield a compound of formula I wherein B represents carboxy and wherein the chain has been extended by 3 carbon atoms.

Furthermore, compounds of formula Ia wherein B' represents halomethyl may be condensed with e.g. the 3-lithio derivative of propiolic acid (prepared with e.g. lithium diisopropylamide) to yield a compound of formula I wherein A contains a terminal alkynylene, B represents carboxy and the chain length has been extended by 3 carbon atoms.

Compounds of formula Ia wherein A represents lower alkylene or a direct bond and B represents a reactive functional derivative of hydroxymethyl, such as halomethyl, may be condensed with a lower alkanol (or thiol), or a phenol (or thiophenol) appropriately substituted by B, preferably in the presence of a strong base, to give compounds of formula I wherein A represents lower alkylene-(thio or oxy)-phenylene, phenylene-(thio or oxy)-lower alkylene or lower alkylene-(thio or oxy)-lower alkylene.

Hydrolysis of intermediates of formula Ia wherein B' represents trialkoxymethyl to compounds of formula I wherein B is carboxy is advantageously carried out with inorganic acids such as hydrohalic or sulfuric acid. Hydrolysis of intermediates wherein B' represents etherified hydroxymethyl to compounds of formula I wherein B represents hydroxymethyl is preferably carried out with solutions of inorganic acids such as a hydrohalic acid.

The compounds of formula Ia wherein B' is halomethyl are converted to compounds of formula I, wherein B is carboxy and the chain length is extended by two carbons, by first treating with e.g. a di(lower)alkylmalonate followed by hydrolysis and decarboxylation under standard conditions.

More specifically, the intermediates of formula Ia wherein B' is halomethyl, such as chloromethyl, are converted to compounds of formula I, wherein B is carboxy and the chain length is extended by two carbons, by first treating with e.g. a di(lower) alkyl malonate, such as diethyl malonate, in the presence of a base, such as potassium carbonate or sodium ethoxide, in a solvent such as dimethylformamide, preferably at a temperature range from 50° to 100°. The resulting substituted di(lower)alkyl malonate is hydrolyzed, advantageously with an aqueous base, such as dilute sodium hydroxide, to the corresponding malonic acid which is decarboxylated e.g. by heating in xylene solution, to give a compound of formula I wherein B is carboxy. Replacement of the di(lower)alkyl malonate with a lower alkyl cyanoacetate yields the corresponding compounds of formula I wherein B is cyano.

Compounds of the invention, wherein A represents straight chain or branched alkenylene with a terminal double bond, may also be prepared from intermediates of formula Ia wherein B' is halomethyl. For instance, said intermediates are first treated with e.g. a lower alkyl ester of an α-(aryl- or alkyl) thioacetic acid such as ethyl α-(phenylthio)-acetate, in the presence of a strong base such as sodium hydride. Subsequent oxidation of the resulting α-arylthio or α-alkylthio substituted substituted ester to the α-arylsulfinyl or α-alkylsulfinyl ester with e.g. sodium periodate, followed by heat-induced elimination, by e.g. refluxing in xylene, yields a compound of general formula I (an α,β-unsaturated ester) wherein A represents alkenylene and B represents e.g. lower alkoxycarbonyl, and the chain length has been extended by two carbon atoms. The same transformation is also carried out using e.g. ethyl α-(phenylseleno)acetate as described in J. Am. Chem. Soc. 95, 6137 (1973). Similarly, the compounds of formula Ia wherein B' represents halomethyl may first be converted to the corresponding carboxaldehydes with e.g. dimethylsulfoxide in the presence of triethylamine and silver tetrafluoroborate, or with chromium trioxide and pyridine in methylene chloride. Subsequent Wittig condensation e.g. with trimethylphosphonacetate or ethyl (triphenylphosphoranylidene)-acetate also yields the above-cited α,β-unsaturated esters.

Compounds of formula I wherein A represents straight chain or branched alkenylene with a terminal double bond, e.g. α,β-unsaturated esters, may also be prepared from the corresponding saturated esters by treatment with e.g. phenylselenyl chloride in the presence of a strong base according to the procedure described in J.Am. Chem. Soc. 95, 6137 (1973).

Intermediates of formula Ia wherein B' is halomethyl may be reacted preferably with a alkali metal cyanide such as potassium cyanide in a conventional manner to yield the compounds of formula I wherein the chain is extended by 1 carbon atom and B is cyano. These in turn are converted to compounds of formula I wherein B is carboxy, alkoxycarbonyl or carbamoyl using methods known to the art.

The conversion of compounds of formula I wherein B represents cyano to compounds of formula I wherein B represents lower alkoxycarbonyl is advantageously carried out by treatment first with a lower alkanol, e.g. anhydrous ethanol, in the presence of a strong acid, e.g. hydrochlorid acid preferably at reflux temperature, followed by careful hydrolysis with water.

Furthermore, the conversion of the said nitriles to compounds of formula I wherein B represents carbamoyl is preferably carried out by treatment with an alkali metal hydroxide, e.g. dilute sodium hydroxide, and hydrogen peroxide, preferably at room temperature.

Compounds of formula I wherein B is lower alkoxycarbonyl may be amidized with ammonia, mono- or di-(lower)alkylamines e.g. methylamine, dimethylamine in an inert solvent, e.g. a lower alkanol, such as butanol, optionally at elevated temperatures to yield compounds of formula I wherein B represents unsubstituted, mono- or di(lower) alkylcarbamoyl.

The compounds of formula I wherein B represents unsubstituted carbamoyl may be dehydrated to the corresponding nitriles by methods known to the art.

Conversions of compounds of formula I wherein B is lower alkoxycarbonyl, cyano, unsubstituted, mono- or di-(loweralkyl) carbamoyl to compounds of formula I wherein B represents carboxy is advantageously carried out by hydrolysis with inorganic acids such as hydrohalic or sulfuric acid or with aqueous alkalies, preferably alkali metal hydroxides such as lithium or sodium hydroxide.

Compounds of formula I wherein B represents carboxy or lower alkoxycarbonyl may be reduced with simple or complex light metal hydrides such as lithium aluminium hydride, alane or diborane to compounds of formula I wherein B is hydroxymethyl. Said alcohols are also obtained by appropriate solvolysis of compounds of formula Ia wherein B' is halomethyl by treatment with e.g. an alkali metal hydroxide such as lithium or sodium hydroxide.

Said alcohols may in turn be transformed to the compounds of formula I wherein B is carboxy with conventional oxidizing agents, advantageously with pyridinum dichromate in dimethylformamide at room temperature.

Free carboxylic acids may be esterified with lower alkanols such as ethanol in the presence of a strong acid, e.g. sulfuric acid, advantageously at elevated temperature or with diazo (lower) alkanes, e.g. diazomethane in a solvent such as ethyl ether, advantageously at room temperature, to give the corresponding esters, namely compounds of formula I wherein B is lower alkoxycarbonyl.

Furthermore, the free carboxylic acids may be converted via treatment of a reactive intermediate thereof, e.g. an acyl halide such as the acid chloride, or a mixed anhydride, e.g. such derived from a lower alkyl halocarbonate such as ethyl chloroformate, with ammonia, mono- or di-(lower) alkylamines, in an inert solvent such as methylene chloride, preferably in the presence of a basic catalyst such as pyridine, to compounds of formula I wherein B represents unsubstituted, mono or di-(lower)-alkylcarbamoyl.

Compounds of formula I wherein B represents mono(lower)-alkylcarbamoyl are converted to compounds of formula I wherein B is di(lower)alkyl-carbamoyl by treatment of the former with a strong base e.g. sodium hydride followed by an alkylating agent, e.g. a lower alkyl halide in an inert solvent, e.g. dimethylformamide.

Furthermore compounds of formula I wherein A represents a straight chain or branched alkynylene or alkenylene may be converted by catalytic hydrogenation, advantageously under neutral conditions e.g. with palladium catalyst at atmospheric pressure in an inert solvent, e.g. ethanol, to compounds of formula I wherein A represents straight chain or branched alkylene.

The carboxaldehydes, the compounds of formula I wherein B represents formyl, may be prepared by oxidizing compounds of formula I or Ia wherein B represents hydroxymethyl or B' represents halomethyl with e.g. dimethyl sulfoxide and a catalyst, such as a mixture of triethylamine and silver tetrafluoroborate, or with chromium trioxide and pyridine or other oxidizing agents known in the art. Said carboxaldehydes are converted to the corresponding acetals, the compounds of formula Ia wherein B' represents di(lower)alkoxymethyl, or alkylenedioxymethyl e.g. a dimethylacetal, by acid-catalyzed condensation with an alcohol, e.g. methanol.

Compounds of formula I wherein B represents carboxy may be converted by the well-known Arndt-Eistert synthesis to compounds of formula I wherein B represents carboxy and the chain has been extended by 1 carbon atom. More particularly, a reactive functional derivative of the starting carboxylic acid, e.g. the acid chloride, is treated with diazomethane in e.g. diethyl ether to yield a compound of formula Ia wherein B' represents diazoacetyl. Rearrangement with e.g. silver oxide yields said carboxylic acid of formula I wherein the chain has been extended by 1 carbon atom.

The compounds of formula I wherein B represents hydroxycarbamoyl (hydroxamic acids) may be prepared by condensing a compound of formula I, wherein B represents carboxy or a reactive functional derivative thereof, lower alkoxycarbonyl or carbamoyl, with hydroxylamine or an acid addition salt thereof in the presence of a basic reagent, e.g. sodium hydroxide. Said condensation is carried out according to methods known per se e.g. as described in Barton et al., Comprehensive Organic Chemistry, Vol. 2 pp. 1037–1038 (1079), preferbly under basic conditions advantageously with hydroxylamine hydrochloride, in an inert polar solvent, e.g. a lower alkanol such as ethanol, preferably at a temperature range of about 0° to 50°, advantageously at room temperature.

The compounds of formula I wherein B represents 5-tetrazolyl may be prepared by condensing a compound of formula I, wherein B represents preferably cyano, with hydrazoic acid or a compound which serves as a source of hydrazoic acid, e.g. a metal or ammonium salt of hydrazoic acid, preferably an alkali metal azide such as sodium azide or ammonium azide. Said condensation is carried out according to methods known per se, e.g. as described in Barton et al., Comprehensive Organic Chemistry Vol. 4, pp. 407–409 (1979), preferably in a solvent such as dimethylformamide and at an elevated temperature ranging from about 50° to 200°, advantageously 75° to 150°, and in the presence of an acid, e.g. hydrochloric acid or ammonium chloride.

Said tetrazoles may also be prepared from a compound of formula I wherein the group B representing cyano or carbamoyl is first converted to a (halo or lower alkoxy)-iminocarbonyl group for condensation with e.g. an alkali metal azide or ammonium azide.

The compounds of formula Ia wherein B' represents 4,5-dihydro-2-oxazolyl are preferably prepared by condensing a compound of formula I, wherein B represents carboxy or a reactive functional derivative thereof, lower alkoxycarbonyl or carbamoyl, with 2-hydroxyethylamine or with aziridine. The condensation is carried out according to methods generally known per se, e.g. as described in J. Organic Chemistry 39, 2787 (1974), preferably in an inert solvent such as toluene at a temperature range of about 25°–100°. Said condensation occurs either spontaneously or in the presence of condensing agents, e.g. disubstituted carbodiimides, such as dicyclohexylcarbodiimide, in the case where B represents carboxy.

The above-mentioned reactions are carried out according to standard methods, in the presence or absence of diluents, preferably such as are inert to the reagents and are solvents thereof, of catalysts, condensing or said other agents respectively and/or inert atmospheres, a low temperatures, room temperature or elevated temperatures preferably at the boiling point of the solvents used, and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof,or in which the starting materials are formed under the reaction conditions, or in which the reaction components are used in the form of their salts or optically pure antipodes.

Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of optical isomers such as racemates, mixtures of diastereoisomers, mixtures of racemates or mixtures of geometrical isomers. The aforesaid possible isomers or mixtures thereof are within the purview of this invention; certain particular isomers may be preferred.

Any resulting mixtures of diastereoisomers, mixtures of racemates and geometric isomers can be separated on the basis of the physicochemical differences of the constituents, in known manner, into the pure isomers, diastereoisomers, racemates, or geometric isomers, for example by chromatography and/or fractional crystallisation.

Any resulting racemates can be resolved into the optical antipodes by known methods, for example by e.g. reacting an acidic end product with an optically active base that forms salts with the racemic acid, and separating the salts obtained in this manner, for example by fractional crystallization, into the diastereoisomeric salts from which the optically active carboxylic acid antipodes can be liberated on acidification. The basic racemic products can likewise be resolved into the optical antipodes, e.g. by separation of the diastereoisomeric salts thereof, with an optically active acid, and liberating the optically active basic compound by treatment with a standard base. Racemic products of the invention can thus be resolved into their optical antipodes, e.g., by the fractional crystallisation of d- or l-(tartrates, mandelates, camphorsulfonates) or of d- or l-(α-methylbenzylamine, cinchonidine, cinchonine, quinine, quinidine, ephedrine, dehydroabietylamine, brucine or strychnine) salts. Advantageously, the more active of the two antipodes is isolated.

Finally the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein B represents carboxy can thus also be converted into the corresponding metal or ammonium salts. These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, and parenteral administration to mammals, including man, for the treatment or prevention of diseases responsive to inhibition of thromboxane synthetase, comprising an effective amount of a pharmacologically active compound of formula I, or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders, e.g. magnesium aluminium silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To a suspension of 60% sodium hydride (0.34 g) in dimethylformamide (10 ml), while stirring under nitrogen at 0°–5°, is added dropwise a solution of 2-(1-imidazolyl)-3-methyl-indole (1.50 g) in dimethylformamide (15 ml). Upon complete addition the mixture is stirred at 0°–5° for 1 hour. To the nearly complete solution is added methyl 6-bromohexanoate (1.67 g) dropwise. The mixture is stirred at 0°–5° for 0.5 hour, then for two days at room temperature. The solution is poured into water (100 ml) and extracted with ethyl acetate (3×50 ml), dried (MgSO$_4$), filtered, and concentrated in vacuo to give an amber oil which is stirred with 100 ml of petroleum ether for 15 minutes. The mixture is placed in a separatory funnel and the insoluble amber oil separated and removed. The oil is dried in vacuo to give 1-(5-methoxycarbonylpentyl)-2-(1-imidazolyl)-3-methylindole as an oil; NMR (CDCl$_3$): δ3.60 (3H), 3.90 (2H).

The indole starting material is prepared as follows: To a solution of 3-methylindole (7.87 g) and imidazole (20.42 g) in dioxane (350 ml) stirring at 10° is added a solution of bromine (3.1 ml) in dioxane (125 ml) dropwise over a period of 25 hours. Upon complete addition, the cooling bath is removed and the resulting yellow suspension is allowed to warm to room temperature while stirring overnight. The solid which had formed is removed by vacuum filtration. The filtrate is concentrated in vacuo to give an amber oil. This oil is suspended in 2N HCl (100 ml) and washed with ether (3×100 ml). The acidic layer is made basic to pH 10 with 3N NaOH and extracted with ether (6×100 ml). The ether extract is dried (MgSO$_4$), filtered and concentrated in vacuo to give a partially crystalline residue. This residue is triturated with petroleum ether/ether and the solid which results is collected and recrystallised from acetonitrile (30 ml) to give 2-(1-imidazolyl)-3-methylindole, m.p. 156°–158°.

Methyl 6-bromohexanoate is prepared as follows: A solution of 6-bromohexanoic acid (10 g) in 50 ml of methanol to which was added 1.0 ml of concentrated sulfuric acid is heated under reflux for 8 hours. The methanol is distilled off, the residue is dissolved in ether. The ether solution is washed free of acid with water, dried over sodium sulfate and evaporated to dryness. Distillation at 0.8 mm Hg gives methyl 6-bromohexanoate, b.p. 85°–90°/0.8 mm.

EXAMPLE 2

In a similar manner is prepared 1-(4-ethoxycarbonylbutyl)-2-(1-imidazolyl)-3-methylindole; NMR (CDCl$_3$): 1.20 (3H), 4.07 (2H), 3.90 (2H).

EXAMPLE 3

A mixture of 1-(5-methoxycarbonylpentyl)-2-(1-imidazolyl)-3-methylindole (1.80 g) and 30 ml of 3N NaOH is stirred at room temperature for 1.3 hours. The resulting clear, yellow solution is neutralized to pH 6 with 2N HCl. The resulting suspension is extracted with ethyl acetate (2×50 ml). The organic extract is washed with a saturated NaCl solution (1×25 ml), dried (MgSO$_4$), filtered, and concentrated in vacuo to give a cream-colored solid. The solid is dissolved in ethanol and the solution treated with 0.6 ml of 6.5N HCl in ethanol. The solution is diluted with diethyl ether and after standing for several hours the precipitate which forms is collected by filtration to give 1-(5-carboxypentyl)-2-(1-imidazolyl)-3-methylindole hydrochloride, m.p. 177.5°–180.5° decomposition.

EXAMPLE 4

In a similar manner is prepared 1-(4-carboxybutyl)-2-(1-imidazolyl)-3-methylindole hydrochloride, m.p. 204°–206°.

EXAMPLE 5

Compounds of formula II in which Im represents 1-imidazolyl which are prepared by the methods described herein.

| Compound | R'$_1$ | R'$_2$ | C$_m$H$_{2m}$ | R$_4$ |
|---|---|---|---|---|
| 5/1 | CH$_3$ | 5-Cl | (CH$_2$)$_5$ | OH |
| 5/2 | CH$_3$ | 5-OCH$_3$ | (CH$_2$)$_5$ | OH |
| 5/3 | CH$_3$ | 5-CH$_3$ | (CH$_2$)$_5$ | OH |
| 5/4 | CH$_3$ | H | (CH$_2$)$_7$ | OH |

-continued

| Compound | R'₁ | R'₂ | CmH2m | R₄ |
|---|---|---|---|---|
| 5/5 | H | H | (CH₂)₅ | OH |

The starting ethyl or methyl ω-bromo esters are obtained commercially or were prepared from the commercially available ω-bromoacids as illustrated above for methyl 6-bromohexanoate.

Methyl 8-bromooctanoate is prepared from azelaic acid essentially as described in U.S. Pat. No. 3,852,419, or by direct esterification of 8-bromooctanoic acid as follows:

Methanol (4.7 L), 8-bromooctanoic acid (0.912 kg) and sulfuric acid (0.912 L) are charged into a suitable reactor and the mixture is heated in reflux temperature for 5 hours and is then stirred at ambient temperature overnight. The solvent is removed at reduced (3 mm Hg) pressure and the oily residue is dissolved in ether (4 L). The solution is washed with water (3×2 L), saturated NaHCO₃ solution (1 L) and brine (1 L). The ether portion is dried (MgSO₄) and filtered to remove dessicant. Evaporation of solvent followed by distillation of the crude oil gives methyl 8-bromooctanoate, b.p. 73°-76°/0.05 mm Hg, $n_D^{23}$ 1.4614.

EXAMPLE 6

Compounds of formula III wherein Im represents 1-imidazolyl, which are prepared according to the methods described herein.

| Compound | R"₂ | C_qH2q | X | R₅ |
|---|---|---|---|---|
| 6/1 | H | CH₂CH₂ | O | OEt |
| 6/2 | H | CH₂CH₂ | O | OH |
| 6/3 | H | CH₂CH₂ | S | OEt |
| 6/4 | H | CH₂CH₂ | S | OH |
| 6/5 | H | CH₂ | bond | OH |
| 6/6 | 5-Cl | CH₂CH₂ | O | OH |
| 6/7 | 5-OCH₃ | CH₂ | bond | OH |
| 6/8 | 5-CH₃ | CH₂CH₂ | O | OH |

The preparation of ethyl p-(2-bromethoxy)-benzoate, the intermediate of formula V required for the synthesis of compounds 6/1, 6/2, 6/6 and 6/8 is described in U.S. Pat. No. 2,790,825. The corresponding thio starting material can be similarly prepared and used for compounds 6/3 and 6/4. The nitrile, 1-(4-cyanobenzyl)-3-methyl-2-(1-imidazolyl)indole is prepared starting from the known p-cyanobenzyl bromide. Subsequent hydrolysis with a mixture of aqueous hydrochloric acid and glacial acetic acid yields the compound of example 6/5.

EXAMPLE 7

Treatment of 1-(5-methoxycarbonylpentyl)-2-(1-imidazolyl)-3-methylindole with lithium aluminium hydride in tetrahydrofuran at room temperature yields 1-(6-hydroxyhexyl)-2-(1-imidazolyl)-3-methylindole.

EXAMPLE 8

A solution of 4 g of 1-(4-methoxycarbonylbutyl)-3-methyl-2-(1-imidazolyl)indole in 40 ml of n-butanol is saturated with ammonia and heated on a steam bath in a pressure bottle for 3 days. The reaction mixture is evaporated to dryness and the product is crystallized to yield the 1-[4-carbamoylbutyl]-3-methyl-2-(1-imidazolyl)indole.

EXAMPLE 9

2-(p-Ethoxycarbonylphenoxy)-1-chloroethane is added in one portion to a mixture of 2-(1-imidazolyl)-3-methylindole (1.97 g), potassium hydroxide (0.62 g) and tetrabutylammonium bromide (0.32 g) in acetonitrile (250 ml) while stirring under nitrogen at room temperature. After stirring at room temperature for 65 hours an additional 0.64 g of tetrabutylammonium bromide is added and the mixture is refluxed for 41 hours. The reaction mixture is cooled to room temperature and filtered. The filtrate is concentrated in vacuo and the oil obtained dissolved in ethyl acetate and extracted with 1N hydrochlorid acid. The aqueous extract is made basic to pH 10 with 3N sodium hydroxide and extracted with ethyl acetate (3×100 ml). This extract is dried over magnesium sulfate, filtered, and concentrated in vacuo to give a crude oil which is purified by flash chromatography on silica gel. The product is eluted with 3% methanol in methylene chloride to give 1-[2-(p-ethoxycarbonylphenoxy)-ethyl]-2-(1-imidazolyl)-3-methylindole; NMR (CDCl₃): δ8.02 (d, 2H), 7.87-7.13 (m, 7H), 6.80 (d, 2H), 4.50-4.00 (m, 6H), 2.20 (s, 3H), 1.37 (t, 3H).

EXAMPLE 10

A solution of 1-[2-(p-ethoxycarbonylphenoxy)-ethyl]-2-(1-imidazolyl)-3-methylindole (1.66 g) and 3N sodium hydroxide (20 ml) in absolute ethanol (20 ml) is stirred and refluxed for 2 hours. The solution is cooled and acidified to pH 3 with 3N hydrochlorid acid. The precipitate which forms (m.p.>300°) is collected. This solid is dissolved in a saturated sodium bicarbonate solution and the carboxylic acid is reprecipitated by acidifying the solution to pH 5 with 3N hydrochloric acid. The white solid is collected to give 1-[2-(p-carboxyphenoxy)-ethyl]-2-(1-imidazolyl)-3-methylindole; NMR (DMSO): δ2.17 (s, 3H), 4.30 (m, 4H).

EXAMPLE 11

A solution of 5-methoxy-3-methyl-2-(1-imidazolyl)indole (0.57 g) in dimethylformamide (4 ml) is added dropwise to a suspension of sodium hydride (50% dispersion in mineral oil), 0.27 g in dimethylformamide (5 ml) while stirring under N₂ at 0°-5°. The mixture is stirred at 5° for ½ hour. A solution of 6-bromohexanoic acid (0.55 g) in dimethylformamide (4 ml) is added dropwise to the reaction mixture while stirring at 0°-5°. The mixture is stirred at 0°-5° for ½ hour and then overnight at room temperature. The thick suspension is diluted with water (50 ml) and the mixture is washed with ether (2×25 ml). The aqueous layer is acidified to pH 5.6 with 1N hydrochloric acid and extracted with ethyl acetate (3×30 ml). The organic extract is dried over magnesium sulfate, filtered, and concentrated in vacuo to give an oil which becomes partially crystalline. This material is triturated with ether and the solid is collected to give 1-(5-carboxypentyl)-5-methoxy-3-methylindole, m.p. 134°-137°.

A solution of 5-methoxygramine (3.96 g) in absolute ethanol (80 ml) with 10% Palladium on carbon (0.40 g) is hydrogenated at atmospheric pressure for 10 hours. The catalyst is removed by vacuum filtration through Hy-Flo and the filtrate is concentrated in vacuo to give an oil which crystallizes on standing to give 5-methoxy-3-methylindole.

A solution of bromine (0.62 ml) in dioxane (25 ml) is added dropwise over a period of 2 hours to a mixture of 5-methoxy-3-methylindole (2.00 g) and imidazole (4.08 g) in dioxane (50 ml) while stirring at 10°. Upon complete addition cooling bath is removed and the suspension is stirred two days at room temperature. The mixture is concentrated in vacuo and the oil obtained is suspended in ether (100 ml) and extracted into 1N hydrochloric acid (2×50 ml). The acid extract is first washed with ether (1×50 ml), the pH is adjusted to pH 6 with 3N sodium hydroxide (38 ml), and the aqueous mixture is then extracted with ether (8×50 ml). This extract is dried over magnesium sulfate, filtered, and concentrated in vacuo to give an oil. This oil is purified by flash chromatography on silica gel (eluent: 95% methylene chloride, 5% methanol) to give 2-(1-imidazolyl)-5-methoxy-3-methylindole as a crystalline solid; NMR (CDCl$_3$): δ10.4 (s, 1H), 7.67 (s, 1H), 3.88 (s, 3H), 2.22 (s, 3H).

EXAMPLE 12

A solution of 5-chloro-2-(1-imidazolyl)-3-methylindole (0.37 g) in anhydrous dimethylformamide (4 ml is added dropwise to a suspension of a 50% dispersion of sodium hydride in mineral oil (0.17 g) in anhydrous dimethylformamide (3 ml) while stirring under nitrogen at 0°. The mixture is stirred at 0° for ½ hour. To the suspension is then added a solution of 6-bromohexanoic acid (0.35 g) in anhydrous dimethylformamide (4 ml) dropwise. The reaction mixture is stirred at 0° for ½ hour and then at room temperature for several hours. The resulting suspension is diluted with water (30 ml) and washed with ether (2×15 ml). The aqueous solution is acidified to pH 5 with 1N hydrochloric acid and extracted with ether (3×30 ml). The extract is dried over magnesium sulfate, filtered and concentrated in vacuo to give an oil which crystallizes. This material is dissolved in ethanol (3 ml) and the solution is treated with 0.11 ml of 7N ethanolic hydrogen chloride. The solution is concentrated in vacuo and the residue is triturated with ether. The hydrochloride salt is collected and is purified by recrystallization from acetonitrile/ether to give 1-(5-carboxypentyl)-5-chloro-2-(1-imidazolyl)-3-methylindole hydrochloride, m.p. 149°-152°.

The starting material is prepared as follows: 5-Chloroindole (4.00 g) is added to a mixture of 40% aqueous dimethylamine (4.5 ml), and 37% aqueous formaldehyde (2.6 ml) in glacial acetic acid (6.4 ml) while stirring at 10°. The cooling bath is removed and the mixture stirred at room temperature for 3 hours. The mixture is made basic with ammonium hydroxide whereupon a precipitate is formed. The solid is collected, washed with water and dried to give 5-chloro gramine, m.p. 149°-151°.

Acetic acid (1.02 g) is added to a suspension of 5-chlorogramine (1.80 g), in a 1:1 mixture of ethanol and toluene (9 ml) while stirring at room temperature. To the resulting solution is added a solution of dimethylsulfate (5.42 g), in toluene (6 ml) dropwise. The solution is kept at 0° for 45 hours. The solution is diluted with toluene (10 ml) and the mixture is placed in a separatory funnel. After standing a few hours an oil separates. This is collected, dried in vacuo and dissolved in water. To the aqueous solution is added a solution of potassium iodide (7.47 g) in water (11 ml). The mixture is stirred for several minutes, then allowed to separate. The supernatant is decanted from the oil which forms. This process is repeated with 10 ml of water. The oil which remains is treated with 5 ml of a 3:1 ethyl acetate/acetone solution and stirred briefly. The solid which forms is collected by vacuum filtration to give the quaternary salt, 5-chloroindole-3-methyltrimethylammonium iodide.

The quaternary salt (1.62 g) is added to a suspension of lithium aluminium hydride (0.72 g) in dry tetrahydrofuran (75 ml) while stirring under nitrogen at room temperature. The mixture is refluxed for 24 hours. The suspension is cooled and poured slowly into ice. The aqueous mixture is diluted with 10 ml of a saturated ammonium chloride solution and extracted with ether (3×100 ml). The extract is washed with a saturated sodium chloride solution, dried over magnesium sulfate, filtered, and concentrated in vacuo to give an oil which becomes partially crystalline and is triturated with hexane to give 5-chloro-3-methylindole.

Condensation of 5-chloro-3-methylindole with imidazole according to the procedure described in the previous examples gives 5-chloro-2-(1-imidazolyl)-3-methylindole, m.p. 212°-215°.

EXAMPLE 13

A solution of 3-methyl-2-(1-imidazolyl)indole (1.50 g) in dimethylformamide (10 ml) is added dropwise to a suspension of 50% sodium hydride dispersion in mineral oil (0.77 g) in dimethylformamide (20 ml) stirred under nitrogen at 5°-10°. The suspension is stirred at 5°-10° for ½ hour. A solution of α-bromotoluic acid (1.63 g) in dimethylformamide (5 ml) is added dropwise to the suspension. The suspension is again stirred at 5°-10° for ½ hour and then overnight at room temperature. The suspension is diluted with water (100 ml) and acidified to pH 6 to 7 with 1N hydrochloric acid. The white precipitate which forms is collected by vacuum filtration, washed with water and dried to give 1-(p-carboxybenzyl)-2-(1-imidazolyl)-3-methylindole, m.p. 221°-5°. Recrystallization from acetonitrile gives crystals melting at 225°-7°.

EXAMPLE 14

3-Methyl-2-(1-imidazolyl)indole (0.78 g) in dimethylformamide (8 ml) is added dropwise to a suspension of sodium hydride (50% dispersion in mineral oil, 0.20 g) in dimethylformamide (8 ml) stirred under nitrogen at 5°-10°. The resulting solution is stirred at 5°-10° for ½ hour. A solution of ethyl 8-bromooctanoate (1.00 g) in dimethylformamide (5 ml) is added dropwise. The reaction mixture is stirred at 5°-10° for ½ hour and then overnight at room temperature. The mixture is diluted with water (50 ml) and extracted into methylene chloride (3×25 ml). The extract is washed with water and saturated aqueous sodium chloride solution, dried over MgSO$_4$, filtered, and concentrated in vacuo to give a two-phase oil. This oil is dissolved in ether (50 ml) and the solution is washed with water (5×25 ml) to remove dimethylformamide. The ether layer is dried over MgSO$_4$, filtered, and concentrated in vacuo to give 1-(7-ethoxycarbonylheptyl)-2-(1-imidazolyl)-3-methylindole a viscous oil; NMR (CDCl$_3$): δ 4.12 (q, 2H), 3.82 (t, 2H), 2.20 (s, 3H), 1.23 (t, 3H).

EXAMPLE 15

A mixture of 1-(7-ethoxycarbonylheptyl)-2-(1-imidazolyl)-3-methylindole (0.75 g), absolute ethanol (2 ml), and 3N sodium hydroxide (10 ml) is stirred at room temperature for 18 hours. The resulting clear solution is concentrated in vacuo and the residue obtained is diluted with water (40 ml) and acidified to pH 5.9 with 1N hydrochloric acid. The mixture is extracted with ethyl acetate (3×25 ml) and the extract is washed with saturated sodium chloride solution, dried over magnesium sulfate, filtered, and concentrated in vacuo to give an oil which crystallizes on standing. The solid is purified by trituration with ether (10 ml) to give 1-(7-carboxyheptyl)-2-(1-imidazolyl)-3-methylindole; m.p. 101°–103°.

EXAMPLE 16

To a suspension of 3.0 g of 50% sodium hydride in mineral oil in 40 ml of dimethylformamide under nitrogen at 0°–5° is added dropwise over 20 minutes a solution of 10.0 g of 3-methyl-2-(1-imidazolyl)indole in 60 ml of dimethylformamide. The mixture is stirred for 0.5 hour at 0°–5° followed by the dropwise addition of 17.5 g of 1-tetrahydropyranyloxy-8-bromooctane in 50 ml of dimethylformamide. After stirring at 0°–10° for 1 hour and at room temperature for 0.5 hour, the reaction mixture is poured into ice-water and extracted with ether. The ether extract is washed with water, dried over MgSO$_4$ and evaporated to dryness. The residue is dissolved in 100 ml of 3N hydrochloric acid, the resulting mixture is kept at room temperature for 0.5 hour, washed with ether, basified with aqueous 3N sodium hydroxide solution and extracted with methylene chloride. The methylene chloride solution is evaporated to dryness to give 1-(8-hydroxyoctyl)-2-(1-imidazolyl)-3-methylindole.

EXAMPLE 17

A solution of 4 g of 1-(7-ethoxycarbonylheptyl)-3-methyl-2-(1-imidazolyl)indole in 40 ml of n-butanol is saturated with methylamine and heated on a steam bath in a pressure bottle for 3 days. The reaction mixture is evaporated to dryness to yield 1-[7-(N-methylcarbamoyl)heptyl]-3-methyl-2-(1-imidazolyl)indole.

EXAMPLE 18

A solution of 50 mg of 1-(4-carbamoylbutyl)-3-methyl-2-(1-imidazolyl)indole in 1 ml of 6N HCl is heated at reflux temperature for 3 hours. The reaction mixture is concentrated to dryness to give 1-(4-carboxybutyl)-3-methyl-2-(1-imidazolyl)indole hydrochloride.

EXAMPLE 19

To a solution of Collins Reagent prepared with chromium trioxide (5.6 g) and pyridine (8.86 g) in dichloromethane (150 ml) at 0°–5° under a nitrogen atmosphere is added all at once 1.8 g of 1-(6-hydroxyhexyl)-3-methyl-2-(1-imidazolyl)-indole in dichloromethane (15 ml). The mixture is stirred for an additional 25 minutes, then filtered through celite. The filtrate is then passed through a silica gel column. The product is eluted from the silica gel with a 1:1 mixture of ethyl acetate:dichloromethane (500 ml). Concentration in vacuo yields 1-(5-formylpentyl)-2-(1-imidazolyl)-3-methylindole.

EXAMPLE 20

Trimethyl phosphonoacetate (328 mg) is added dropwise to a solution of potassium tert-butoxide (220 mg) in tetrahydrofuran (5 ml) of 0° under a nitrogen atmosphere. The solution is stirred at 0° for 20 minutes, then cooled to −78°. A solution of the aldehyde, 1-(5-formylpentyl)-2-(1-imidazolyl)-3-methylindole (450 mg) in tetrahydrofuran (5 ml) is added dropwise over 15 minutes. The mixture is kept at −78° for 15 minutes, then the cooling bath is removed. The mixture is stirred overnight at room temperature, then diluted with water (25 ml) and extracted with ethyl acetate (3×25 ml). The combined extracts are washed with saturated sodium bicarbonate, then brine, and dried over anhydrous magnesium sulfate. Concentration in vacuo yields the α,β-unsaturated ester 1-(7-methoxycarbonylhept-6-enyl)-2-(1-imidazolyl)-3-methylindole.

EXAMPLE 21

Hydrolysis of 50 mg of 1-(7-methoxycarbonylhept-6-enyl)-2-(3-pyridyl)-3-methylindole 1N aqueous lithium hydroxide (1 ml) yields 1-(7-carboxyhept-6-enyl)-2-(1-imidazolyl)-3-methylindole.

EXAMPLE 22

1-(7-Carboxyhept-6-enyl)-2-(1-imidazolyl)-3-methylindole (20 mg) is dissolved in 1 ml of absolute ethanol with a catalytic amount of 10% palladium on charcoal and hydrogenated at 1 atmosphere pressure. After one mole of hydrogen is consumed the catalyst is removed by filtration and washed with a few milliliters of ethanol. The combined filtrates are concentrated to yield the 1-(7-carboxyheptyl)-3-methyl-2-(1-imidazolyl)indole.

EXAMPLE 23

A solution of 3-methyl-2-(1-imidazolyl)-indole (2.0 g) in 12 ml of dimethylformamide is added to a suspension of 0.6 g of 50% sodium hydride (dispersion in mineral oil) in 6 ml of dimethylformamide at 0°. The mixture is stirred at 0° for 0.5 hour and is treated with a solution of 1.8 g of 5-bromovaleronitrile in 4 ml of dimethylformamide. This mixture is stirred at room temperature overnight and is poured into 125 ml of water. This is extracted with 2×50 ml of ethyl acetate, the extract is washed with water and dried over magnesium sulfate to give 1-(4-cyanobutyl)-3-methyl-2-(1-imidazolyl)-indole.

EXAMPLES 24

A mixture of 600 mg of 1-(4-cyanobutyl)-3-methyl-2-(1-imidazolyl)indole, 173 mg of sodium azide, 142 mg of ammonium chloride and 5 mg of lithium chloride in 2 ml of dimethylformamide is heated at 120° overnight. After cooling the mixture is filtered and the filtrate diluted with ca. 25 ml of water. After the pH is adjusted to 10–11 with 3N NaOH, the solution is washed with ether to remove unreacted nitrile. The aqueous phase is adjusted to pH 5–6 with 2N HCl and extracted with ethylacetate. The extract is washed with water, dried over magnesium sulfate and concentrated in vacuo. The solid residue is slurried in petroleum ether and collected to give 1-[4-(5-tetrazolyl)-butyl]-3-methyl-2-(1-imidazolyl)indole.

EXAMPLE 25

A solution of 3-methyl-2-(1-imidazolyl)indole (1.0 g) in 12 ml of dimethylformamide is added to a suspension of 0.5 g of 50% sodium hydride (dispersion in mineral oil) in 6 ml of dimethylformamide under nitrogen at 10°–15°. After complete addition the mixture is stirred at room temperature for 0.5 hour and is treated with a solution of 2.39 g of ethyl 3-(p-chloromethylphenyl)-2-methylacrylate in 5 ml of dimethylformamide dropwise. The resulting mixture is stirred at room temperature overnight and poured in 100 ml of water. The resulting mixture is extracted with ethyl acetate and the organic layer is washed with 100 ml of saturated sodium chloride, dried over magnesium sulfate and evaporated to yield 1-[p-(2-ethoxy-carbonylpropen-1-yl)benzyl]-3-methyl-2-(1-imidazolyl)indole.

Hydrolysis with 2N aqueous hydrochloric acid yields 1-[p-(2-carboxypropen-1-yl)benzyl]-3-methyl-2-(1-imidazolyl)indole.

The starting material is prepared as follows:

To a suspension of 10.0 g of 50% sodium hydride (dispersion in mineral oil) in freshly distilled dimethoxyethane (DME, 350 ml) stirred under nitrogen at 10° is added 53.6 ml of triethyl 2-phosphonopropionate in ca. 40 minutes. The mixture is stirred for 0.5 hour at 10° and for an additional 1.5 hours during which time the temperature is allowed to rise to room temperature. This solution is transferred under nitrogen by cannula to a 500 ml addition funnel and is added dropwise to a solution of terephthalaldehyde (33.53 g) in dry DME (475 ml) over a period of 1 hour at 22°-34°. After addition is complete the reaction mixture is stirred mechanically at room temperature for 2 hours, poured into 1 L of water and extracted with 4×500 ml of ether. The ether extract is washed with a saturated sodium chloride solution (700 ml), dried over magnesium sulfate, filtered, and concentrated in vacuo to give a yellow oil which partially crystallizes on standing. This crude mixture is purified by suspending in petroleum ether and ethyl acetate (93:7). The filtrate, after removal of unreacted dialdehyde, is concentrated in vacuo to give a mixture which is further purified by high pressure liquid chromatography (using petroleum ether/ethyl acetate 93:7). There is obtained pure ethyl 4-formyl-α-methylcinnamate. A solution of the aldehyde (34.80 g) in 820 ml of absolute ethanol is treated with 12.11 g of granular sodium borohydride at room temperature under nitrogen. The resulting mixture is stirred at room temperature for 3 hours (or until all borohydride has dissolved) and then concentrated to ca. 200 ml volume, diluted with 400 ml of water, and extracted with 3×200 ml of ether. The ether extract is washed with 100 ml of water and brine (100 ml), is dried over magnesium sulfate, filtered, and the filtrate concentrated in vacuo to give ethyl 3-(p-hydroxymethylphenyl)-2-methylacrylate. To a solution of this product in 350 ml of methylene chloride is added at room temperature 11.53 ml of thionyl chloride dropwise over 25 minutes. The clear, colorless solution is stirred for 2 hours. The solution is washed with 100 ml of water, 200 ml of saturated sodium bicarbonate, 100 ml of water, and 100 ml of brine. The organic layer after drying and removal of solvent yields ethyl 3-(p-chloromethylphenyl)-2-methylacrylate.

EXAMPLE 26

1-(5-Formylpentyl)-3-methyl-2-(1-imidazolyl)indole (115 mg) is dissolved in dimethylformamide (1.0 ml) and pyridinium dichromate (300 mg) added all at once. The mixture is stirred overnight at room temperature, then diluted with chloroform, and the combined filtrate is extracted with 0.1N aqueous sodium hydroxide (2 ml). The aqueous extract is acidified to about pH 5.5-6.0 and extracted with chloroform. The chloroform extract is dried and concentrated in vacuo. Purification by chromatography on silica gel yields 1-(5-carboxypentyl)-2-(1-imidazolyl)-3-methylindole.

EXAMPLE 27

1-(5-carboxypentyl)-5-chloro-3-methyl-2-(1-imidazolyl)indole hydrochloride (400 mg) dissolved in 7 ml of tetrahydrofuran is warmed and treated with 210 mg of triethylamine. This solution is added dropwise to a solution of 120 mg of ethyl chloroformate in 1 ml of tetrahydrofuran which is cooled to 0°-5°. The reaction mixture is stirred 1 hour at this temperature and filtered to remove triethylamine hydrochloride. The filtrate is treated with a solution of hydroxylamine hydrochloride (75 mg) and sodium hydroxide (45 mg) in 10 ml of methanol. This mixture is stirred 0.5 hour and concentrated to dryness. The residue is treated with 25 ml of ether-methanol (10:1) and filtered. The filtrate is evaporated to dryness leaving an oil which is dissolved in acetone and treated with 6.5N ethanolic hydrogen chloride to give 1-(5-hydroxycarbamoylpentyl)-3-methyl-2-(1-imidazolyl)indole hydrochloride.

EXAMPLE 28

1-[7,7-(bis-methoxycarbonyl)heptyl]-3-methyl-2-(1-imidazolyl)indole (250 mg) is dissolved in methanol (0.5 ml) and 1N aqueous lithium hydroxide (2.0 ml) added. The mixture is stirred at room temperature for 1 hour, then refluxed for 2.5 hours. The clear solution is concentrated to dryness, and the residue dissolved in water and the pH adjusted to about 5.5-6. The product is then extracted into chloroform. Concentration of the chloroform extract (dried over anhydrous magnesium sulfate) yields 1-[7,7-(biscarboxy)-heptyl]-3-methyl-2-(1-imidazolyl)indole.

A sample of the crude dicarboxylic acid (25 mg) is heated with p-xylene (3 ml) containing 0.1N HCl (0.1 ml) for 0.5 hour. The solution is allowed to cool to room temperature and is extracted into aqueous sodium hydroxide. The aqueous phase is separated, and after adjustment of the pH to about 5-6 extracted with ethyl acetate. The organic phase is dried over anhydrous magnesium sulfate and concentrated to give 1-(7-carboxyheptyl)-3-methyl-2-(1-imidazolyl)indole.

The starting material is prepared as follows:

Thionyl chloride (0.36 ml) is combined with 1-(6-hydroxyhexyl)-3-methyl-2-(1-imidazolyl)indole (1.3 g) at 0°. The mixture is then stirred at room temperature for 1 hour. Saturated aqueous sodium bicarbonate is added and the mixture is extracted with dichloromethane. The extract is washed with saturated sodium chloride solution and dried over anhydrous magnesium sulfate. Concentration to dryness and purification by chromatography gives 1-(6-chlorohexyl)-3-methyl-2-(1-imidazolyl)indole.

1-(6-Chlorohexyl)-3-methyl-2-(1-imidazolyl)indole (0.5 g) is combined with dimethyl malonate (830 mg), potassium carbonate (830 mg) and dimethylformamide (12.0 ml) and the mixture is heated at 80°-90° for 18 hours under nitrogen. The mixture is poured into ice water (80 ml), and acidified with 1N HCl and washed with ether. The aqueous layer is adjusted to about pH 6 and extracted with ethylacetate. The extract is then dried over anhydrous magnesium sulfate and concentrated to yield a product which is purified by preparative TLC to give 1-[7,7-(bis-methoxycarbonyl)heptyl]-3-methyl-2-(1-imidazolyl)-indole.

EXAMPLE 29

1-(6-Chlorohexyl)-3-methyl-2-(1-imidazolyl)indole (150 mg) in dry tetrahydrofuran (2 ml) is added dropwise to magnesium turnings (12 mg) in dry tetrahydrofuran (2 ml) under a nitrogen atmosphere. A crystal of iodine is added during the addition to initiate the reaction. The mixture is refluxed for 4 hours after the addition is completed, then cooled to 0°, and dry carbon dioxide gas bubbled into the flask with stirring for 15 minutes. The mixture is poured into 5 ml of 1N NaOH and extracted with ether. The aqueous phase is adjusted to about pH 5-6 and extracted with ethyl acetate. The organic phase is dried over anhydrous magnesium sulfate and concentrated to dryness yielding 1-(6-carboxyhexyl)-3-methyl-2-(1-imidazolyl)-indole.

EXAMPLE 30

1-(Prop-2-ynyl)-3-methyl-2-(1-imidazolyl)-indole (85 mg) is dissolved in tetrahydrofuran (2 ml) under a nitrogen atmosphere and the resulting solution cooled to −78°. A solution of n-butyl lithium (0.024 ml, 1.6M in hexane) is added dropwise via syringe over 1 minute. After stirring at −78° for an additional 10 minutes the mixture is quenched with methyl chloroformate (0.031 ml) and allowed to warm to room temperature. The mixture is then poured into saturated sodium chloride and extracted with ether. The ether extract is washed with water and dried over anhydrous magnesium sulfate. Concentration in vacuo yields a product which is purified by preparative TLC to give 1-(3-methoxycarbonyl-prop-2-ynyl)-3-methyl-2-(1-imidazolyl)indole.

The starting material is prepared as follows:

Sodium hydride (50% mineral oil dispersion, 53 mg) is washed with petroleum ether under nitrogen. The washed sodium hydride is suspended in dry dimethylformamide (2 ml) and 3-methyl-2-(1-imidazolyl)indole (190 mg) in dimethylformamide (2 ml) added dropwise. The mixture is stirred an additional 30 minutes followed by the dropwise addition of propargyl bromide (220 mg). The mixture is stirred for an additional 2 hours, poured into ice water, acidified with 1N hydrochloric acid and extracted with ether. The aqueous phase is made basic with sodium bicarbonate and extracted with ether. The ether extract is washed with water and dried over anhydrous magnesium sulfate. Concentration in vacuo yields 1-(prop-2-ynyl)-3-methyl-2-(1-imidazolyl)-indole.

EXAMPLE 31

Treatment of 300 mg of 1-(3-methoxycarbonylprop-2-ynyl)-3-methyl-2-(1-imidazolyl)indole in 10 ml of methanol with 3.0 ml of aqueous 1N lithium hydroxide at room temperature yields 1-(3-carboxyprop-2-ynyl)-3-methyl-2-(3-pyridyl)indole.

EXAMPLE 32

Preparation by methods analogous to those described in the previous examples of additional compounds of formula I wherein $R_1=CH_3$, Im=1-imidazolyl, and B=COOH

| Compound | $R_2, R_3$ | A |
|---|---|---|
| 32/1 | H, H | $CH_2S(CH_2)_2$ |
| 32/2 | H, H | $(CH_2)_2-O-(CH_2)_2$ |
| 32/3 | H, H | $(CH_2)_2-O-(CH_2)_3$ |
| 32/4 | 5-F, H | $(CH_2)_3$ |
| 32/5 | 5,6-diCl | $(CH_2)_5$ |
| 32/6 | 5,6 methylenedioxy | $(CH_2)_4$ |
| 32/7 | 5-OH, H | $(CH_2)_5$ |
| 32/8 | 5-SCH$_3$, H | $(CH_2)_5$ |
| 32/9 | H, H | $CH_2-S-(p)-C_6H_4$ |
| 32/10 | H, H | $(CH_2)_{10}$ |
| 32/11 | H, H | $-CH_2CH=CH-CH_2-$ |
| 32/12 | H, H | $CH_2$ |

The alkylating starting materials for compounds of examples 32/1, 32/2 and 32/3 are described in J. Org. Chem. 34, 2955 (1969), U.S. Pat. No. 3,984,459 and Chem. Abstr. 83, 166177b respectively.

The compound of example 32/7 may be prepared by hydrogenolysis of 1-(5-carboxypentyl)-5-benzyloxy-2-(1-imidazolyl)-3-methylindole, starting with 5-benzyloxy-2-(1-imidazolyl)-3-methylindole.

EXAMPLE 33

Preparation of 10,000 tablets each containing 10 mg of the active ingredient.

| Formula: | |
|---|---|
| 1-(4-carboxybutyl)-3-methyl-2-(1-imidazolyl)-indole hydrochloride | 100.00 g |
| Lactose | 1,157.00 g |
| Corn starch | 75.00 g |
| Polyethylene glycol 6,000 | 75.00 g |
| Magnesium stearate | 18.00 g |
| Purified water | q.s. |

Procedure

All the powders are passed through a screen with openings of 0.6 mm. Then the drug substance, lactose, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1,2 mm openings and compressed into tablets with 6.4 mm diameter, uppers bisected.

EXAMPLE 34

Preparation of 10,000 capsules each containing 25 mg of the active ingredient.

| Formula: | |
|---|---|
| 1-(5-carboxypentyl)-3-methyl-2-(1-imidazolyl)-indole hydrochloride | 250.0 g |
| Lactose | 1,650.0 g |

Procedure

All the powders are passed through a screen with openings of 0.6 mm. Then the drug substance is placed in a suitable mixer and mixed with the lactose until homogeneous. No. 3 capsules are filled with 190 mg, using a capsule filling machine.

Similarly prepared are tablets and capsules comprising as active ingredients 10–100 mg of other compounds of the invention, e.g. those given in the examples herein.

What is claimed is:

1. A compound of the formula (I)

wherein $R_1$ represents hydrogen or lower alkyl; Im represents 1-imidazolyl unsubstituted or substituted by lower alkyl, carboxy, lower alkoxycarbonyl or carbamoyl; $R_2$ and $R_3$ independently represent hydrogen, lower alkyl, halogen, trifluoromethyl, hydroxy, lower alkoxy, lower alkyl-(thio, sulfinyl or sulfonyl); or $R_2$ and $R_3$ together when attached to adjacent carbons represent lower alkylenedioxy; A represents alkylene of 1 to 12 carbon atoms, alkenylene of 2 to 12 carbon atoms, alkynylene of 2 to 12 carbon atoms, lower alkylenephenylene-lower alkylene, lower alkylenephenylene, phenylene-lower alkylene, phenylene, a direct bond, lower alkylene-(thio or oxy)-lower alkylene, (thio or oxy)-phenylene, lower alkylene-(thio- or oxy)-phenylene, phenylene-(thio or oxy)-lower alkylene or phenylene-lower alkylene; B represents hydroxycarbamoyl, 5-tetrazolyl or formyl; the N-oxide thereof; or a pharmaceutically acceptable salt thereof.

2. A compound of claim 1, wherein $R_1$ represents hydrogen or lower alkyl; Im represents 1-imidazolyl; $R_2$ and $R_3$ independently represent hydrogen, lower alkyl, halogen, trifluoromethyl, hydroxy, lower alkoxy, lower alkyl-(thio, sulfinyl or sulfonyl); or $R_2$ and $R_3$ together when attached to adjacent carbons represent lower alkylenedioxy; A represents alkylene of 1 to 12 carbon atoms, alkenylene of 2 to 12 carbon atoms, alkynylene of 2 to 12 carbon atoms, lower alkylenephenylene-lower alkylene, lower alkylenephenylene, phenylene lower alkylene, phenylene, a direct bond, lower alkylene-(thio or oxy)-lower alkylene, lower alkylene-(thio or oxy)-phenylene; B represents hydroxycarbamoyl or 5-tetrazolyl.

3. A compound of claim 1 wherein $R_2$ and $R_3$ independently represent hydrogen, lower alkyl, lower alkoxy or halogen; A represents alkylene of 1 to 12 carbon atoms; and B represents 5-tetrazolyl.

4. A compound of the formula I

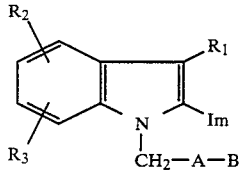

(I)

wherein $R_1$ represents hydrogen or lower alkyl; Im represents 1-imidazolyl unsubstituted or substituted by lower alkyl, carboxy, lower alkoxycarbonyl or carbamoyl; $R_2$ and $R_3$ independently represent hydrogen, lower alkyl, halogen, trifluoromethyl, hydroxy, lower alkoxy, lower alkyl-(thio, sulfinyl or sulfonyl); or $R_2$ and $R_3$ together when attached to adjacent carbons represent lower alkylenedioxy; A represents (thio- or oxy)-phenylene, phenylene-(thio or oxy)-lower alkylene or phenylene-lower alkenylene; B represents carboxy, lower alkoxycarbonyl, carbamoyl, mono- or di-lower alkylcarbamoyl, cyano, hydroxymethyl, hydroxycarbamoyl, 5-tetrazolyl or formyl; the N-oxide thereof; or a pharmaceutically acceptable salt thereof.

5. A compound of claim 4 wherein B represents carboxy, lower alkoxycarbonyl or carbamoyl.

6. A compound of the formula IV

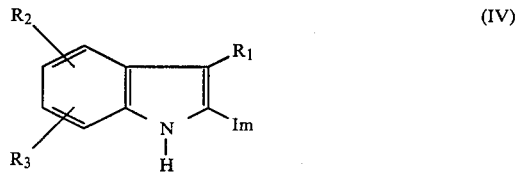

(IV)

wherein $R_1$ represents hydrogen or lower alkyl; Im represents 1-imidazolyl unsubstituted or substituted by lower alkyl, carboxy, lower alkoxycarbonyl or carbamoyl; $R_2$ and $R_3$ independently represent hydrogen, lower alkyl, halogen, trifluoromethyl, hydroxy, lower alkoxy, lower alkyl-(thio, sulfinyl or sulfonyl); or $R_2$ and $R_3$ together when attached to adjacent carbons represent lower alkylenedioxy; or an acid-addition salt thereof.

7. A compound according to claim 6 wherein $R_1$ represents lower alkyl; Im represents 1-imidazolyl; $R_2$ represents hydrogen, lower alkyl, halogen, trifluoromethyl, hydroxy or lower alkoxy; and $R_3$ represents hydrogen.

8. A compound according to claim 6 being 2-(1-imidazolyl)-3-methylindole.

9. A compound according to claim 6 being 5-chloro-2-(1-imidazolyl)-3-methylindole.

* * * * *